United States Patent [19]
Eshhar et al.

[11] Patent Number: 5,906,936
[45] Date of Patent: *May 25, 1999

[54] ENDOWING LYMPHOCYTES WITH ANTIBODY SPECIFICITY

[75] Inventors: Zelig Eshhar, Rehovot; Gideon Gross, Doar Korazin; Tova Waks, Petah Tikva, all of Israel

[73] Assignee: Yeda Research and Development Co. Ltd., Rehovot, Israel

[ * ] Notice: This patent is subject to a terminal disclaimer.

[21] Appl. No.: 08/055,396

[22] Filed: May 4, 1993

Related U.S. Application Data

[63] Continuation of application No. 07/505,277, Apr. 6, 1990, abandoned, which is a continuation-in-part of application No. 07/346,483, May 2, 1989, abandoned.

[30] Foreign Application Priority Data

Jun. 4, 1988 [IL] Israel .......................................... 86278

[51] Int. Cl.$^6$ ........................... C12N 15/13; C07H 21/04; C07K 16/46
[52] U.S. Cl. ................... 435/328; 530/387.3; 536/23.53; 435/69.7; 435/326; 435/330; 435/339; 435/340; 435/342; 435/344; 435/372; 424/93.21; 424/134.1; 424/144.1; 424/184.1
[58] Field of Search .................................... 435/69.7, 326, 435/328, 330, 339, 340, 342, 344, 372; 424/140.1, 134.1, 144.1, 184.1, 93.21; 536/23.53; 530/387.3

[56] References Cited

FOREIGN PATENT DOCUMENTS

| A-180878 | 5/1986 | European Pat. Off. . |
|---|---|---|
| 64-63394 | 9/1989 | Japan . |
| WO-A-8601533 | 3/1986 | WIPO . |

OTHER PUBLICATIONS

Gross et al. Transplantation Proceedings 21(1):127–130 Feb. 1989.
Berke, G. (1991). "Lymphocyte–triggered internal target disintegration", *Immunology Today*, 12(11):396–399.
Kraehenbuehl et al (1991). "Perforin–induced pore formation", *Immunology Today*, 12(11):399–403.
Mariuzza et al (1989). "Secretion of a Homodimeric $V_\alpha C_\kappa$ T–cell Receptor–Immunoglobulin Chimeric Protein", *The Journal of Biological Chemistry*, 264(13):7310–7316.
Ohashi et al (1985). "Reconstitution of an active surface T3/T–cell antigen receptor by DNA transfer", *Nature*, 361:606–609.
Saito et al (1987). "Predictable acquisition of a new MHG recognition specificity following expression of a transfected T–cell receptor β –chain gene", *Nature*, 329:256–259.
Dembic, et al (1986). "Transfer of specificity by murine α and β T–cell receptor genes", *Nature*, 320:232–238.
Linch, et al (1987). "Signal Transduction in Human T Lymphocytes", *Immunological Reviews*, 95: 137–159.

Maloney, et al (1985). "Monoclonal Anti–Idiotype Antibodies Against the Murine B Cell Lymphoma 38C13: Characterization and Use as Probes for the Biology of the Tumor In Vivo and In Vitro", *Hybridoma*, 4(3):191–209.
Ochi et al (1983). "Functional immunoglobulin M production after transfection of cloned immuno–globulin heavy and light chain genes into lymphoid cells", *Proc.Natl.Acad. Sci.USA*, 80:6351–6355.
Wagner, et al (1982). "Dissection of the proliferative and differentiative signals controlling murine cytotoxic T lymphocyte responses", *J. Exp. Med.*, 155:1876–1881.
Weiss, et al (1986). "The Role of the T3/Antigen Receptor Complex in T–Cell Activation", *Ann. Rev. Immunol.*, 4:593–619.
Willingham, et al (1987). "Pseudomonas exotoxin coupled to a monoclonal antibody against ovarian cancer inhibits the growth of human ovarian cancer cells in a mouse model", *Proc. Natl. Acad. Sci. USA*, 84:2474–2478.
Bell (1989). The polymerase chain reaction. *Immunol. Today*, 10, pp. 351–355.
Felgner et al (1987). "Lipofectin: A highly efficient, lipid mediated DNA transfection procedure", *Proc. Natl. Acad. Sci (USA)*, 84:7413.
Potter et al (1984). "Enhancer dependent expression of human x immunoglobulin genes introduced into mouse pre B lymphocytes by electroporation", *Proc. Natl. Acad. Sci. (USA)*, 81:7161.
Gascoigne et al, PNAS 84:2936–2940, 1987 Kimball in *Intro to Immunol.* $2^{nd}$ ed., pp. 9–10, 1983.
Gross et al (1989). "Functional expression of a chimeric T cell receptor with an antibody binding site", In Kaplan et al (eds) "Cellular Basis of Immune Modulation", New York: Alan R. Liss, p. 97.
Gross et al (1989). "Expression of immunoglobulin/T cell chimeric molecules as functional receptors with antibody–type specificity", *Proc. Natl. Acad. Sci. (USA)*, 86:10024.
Kasid et al (1990). "Human gene transfer: Characterizatio of human tumor–infiltrating lymphocytes as vehicles for ret-roviral–mediated gene transfer in man", *Proc. Natl. Acad. Sci. (USA)*, 87:473.

(List continued on next page.)

*Primary Examiner*—Anthony C. Caputa
*Assistant Examiner*—Nancy A. Johnson
*Attorney, Agent, or Firm*—Browdy & Neimark

[57] ABSTRACT

There are produced recombinant gene pairs which endow mononuclear cells, mainly various lymphocyte type cells, with antibody-type specificity. In specific gene pairs the rearranged gene pairs code for a binding site of an antibody molecule from the same species, of the T-cell receptor gene, or another species. Gene pairs of the invention code, for example, for antibodies specific towards tumor-specific antigens, viral antigens, modified self antigens, bacterial or fungal antigens, autoimmune type disease antigens and the like. The invention further relates to expression vectors for the effective transfection of such cell types comprising such a recombinant gene pair, to methods for producing same and to pharmaceutical compositions comprising as active ingredient an effective quantity of lymphocytes transfected with such gene pairs.

33 Claims, 10 Drawing Sheets

OTHER PUBLICATIONS

Kaufmann et al (1981). "Cytotoxic T lymphocyte hybridomas which mediate specific tumor–cell lysis in vitro", *Proc. Natl. Acad. Sci, USA*, 78:2502–2506.

Mullis et al (1987). "Specific synthesis of DNA in vitro via a polymerase–catalysed chain reaction", *Method Enzymol.*, 155:335–350.

Orlandi et al (1989). "Cloning immunoglobulin in variable domains for expression by the polymerase chain reaction", *Proc. Natl. Acad. Sci. (USA)*, 86:3833–3837.

Puri et al (1986). "Antigen–1A interaction and the proteolytic processing of antigen: The structure of the antigen determines its restriction to the A or E molecule of the MMC", *Eur. J. Immunol.*, 16:1093.

Schmitt–Verhulst et al (1978). "H–2–Restricted Cytotoxic Effectors Generated in vitro by the Addition of Trinitrophenyl–Conjugated Soluble Proteins", *J. Exp. Med.*, 147:352–368.

Staerz et al (1985). "Hybrid antibodies can target sites for attack by T Cells", *Nature*, 314:628.

Berke et al (1981). "T Lymphocyte–Mediated Cytolysis. I. A Common Mechanism for Target Recognition in Specific and Lectin–Dependent Cytolysis", *J. Immunol.*, 127:776–781.

Berke et al (1981). "T Lymphocyte–Mediated Cytolysis. II. Role of Target Cell Histo–compatibility Antigens in Recognition and Lysis", *J. Immunol.*, 127:782–787.

Berke et al (1982). "T Lymphocyte–Mediated Cytolysis. I. The Mechanism of CTL–Mediated Cytolysis", in *Adv. Exptl. Biol. Med.*, 146:57–68, eds. Clark, W.R. et al, Plenum Press, New York.

Berke et al (1983). "Cytotoxic T–Lymphocytes: How Do They Function?", *Immunological Rev.*, 72: 5–42.

Clark et al (1982). "T Lymphocyte–Mediated Cytolysis. II. Lytic vs. Nonlytic Interactions of T Lymphocytes", in *Adv. Exptol. Biol. Med.*, 146:69–79, eds. Clark W.R. et al, Plenum Press, N.Y.

Wacholtz et al (1993). Anti–CD3–Stiulated $Ca^{2+}$ Signal in Individual Human Peripheral T *J. Immunol.*, 150:5338–5349.

Young, et al (1987). "A Calcium– and Perforin–Independent Pathway of Killing Mediated by Cytolytic Lymphocytes", *J. Exp. Med.*, 166:1894–1899.

Sambhara et al (1991). "Programmed Cell Death of T Cells Signaled by the T Cell Receptor and the $a_3$ Domain of Class I MHC", *Science*, 252:1424–1427.

Tirosh et al (1985). "Immune Cytolysis Viewed as a Stimulatory Process of the Target", in *Mechanisms of Cell–Mediated Cytotoxicity*, eds. Henkart et al, Plenum Press, New York, pp. 473–492.

Bretscher, P. (1992). "The Two–Signal Model of Lymphocyte Activation Twenty–One Years Later", *Immunolo. Today*, 13(2):74–76.

Henkart, P.A. (1994). "Lymphocyte–Mediated Cytotoxicity: Two Pathways and Multiple Effector Molecules", *Immunity*, 1:343–346.

Jenkins et al (1987). "T–Cell Unresponsiveness in vivo and in vitro: Fine Specificity of Induction and Molecular Characterization of the Unresponsive State", *Immunol. Rev.*, 95:113–135.

Jenkins et al (1987). "Molecular Events in the Induction of a Nonresponsive State in Interleukin 2–Producing Helper T–Lymphocyte Clone", *Proc. Natl. Acad. Sci. (USA)*, 84:5409–5413.

Jenkins, M.K. (1992). "The Role of Cell Division in the Induction of Clonal Anergy", *Immunology Today*, 13(2):69–73.

June et al (1994). "The B7 and CD28 Receptor Families", *Immunology Today*, 15:321–331.

Ostergaard et al (1987). "The Role of $Ca^{2+}$ in Activation of Mature Cytotoxic T Lymphocytes for Lysis", *J. Immunol.*, 139(11):3573–3579.

Romeo et al (1992). "Sequence Requirements for Induction of Cytolysis by the T Cell Antigen/Fc Receptor $\zeta$ Chain", *Cell*, 68:889–897.

Rouvier et al (1993). "Fas Involvement in $Ca^{2+}$–Indendent T Cell–Mediated Cytotoxicity", *J. Exp. Med.*, 177:195–200.

Rudd et al (1994). "Two–Step TCR $\zeta$ CD3–CD4 and CD28 Signaling in T Cells: SH2/SH3 Domains, Protein–Tyrosine and Lipid Kinases", *Immunology Today*, 15:225–234.

Schwartz, R.H. (1990). "A Cell Culture Model for T–Lymphocyte Clonal Anergy", *Science*, 248:1349–1356.

Schwartz, R.H. (1992). "Costimulation of T Lymphocytes: The Role of CD28, CTLA–4, and B7/BB1 in Interleukin–2 Production and Immunotherapy", *Cell*, 2:1065–1068.

Tirosh et al (1985). "T–Lymphocytes–Mediated Cytolysis as an Excitatory Process of the Target", *Cell. Immunol.*, 95:113–123.

Trenn et al (1987). "Exocytosis of Cytolytic Granules May Not Be Required for Target Cell Lysis by Cytotoxic T–Lymphocytes", *Nature*, 330:72–74.

Truneh et al, *Nature* 313:318–320 (1985) Early Steps of Lymphocyte Activation . . .

Lichtenheld et al (1988) *Nature* 335:448–451 "Structure and Function of Human Perforin".

Weiss et al *Advances in Immunology* 41:1–38, (1988) Academic Press Inc. Cell Surface Molecules and Early . . .

*Biochemical and Biophysical Research Communications*, vol. 49, no. 3, Dec. 31, 1987, New York, pp. 960–968; Y. Kuwana et al.; "Expression of Chimeric Receptor Composed of Immunoglobulin–derived V Regions and T–cell Receptor–derived C Regions."

*Schweizerische Medizinische Wochenschrift*, vol. 116, no. 43, 1986, Basel, pp. 1459–1464; J. Cline: "Gene Therapy: Current Status and Future Directions."

*Nature*, vol. 320, Apr. 10, 1986, London, pp. 549–551; C. T. Denny et al: "A Chromosome 14 inversion in a T–cell Lymphoma is Caused by Site Specific Recombination Between Immunoglobulin and T–cell Receptor Loci."

*Cell*, vol. 42, Aug. 1985, New York; pp. 81–87; Yague et al.: "The T–cell Receptor: The Alpha and Beta Chains Define Idotype, and Antigen and MHC Specificity."

*Cell*, vol. 60, no. 6, Mar. 23, 1990, New York, pp. 929–939; Goverman et al.: "Chimeric Immunoglobulin–T Cell Receptor Proteins Form Functional Receptors: Implications for T Cell Receptor Complex Formation and Activation."

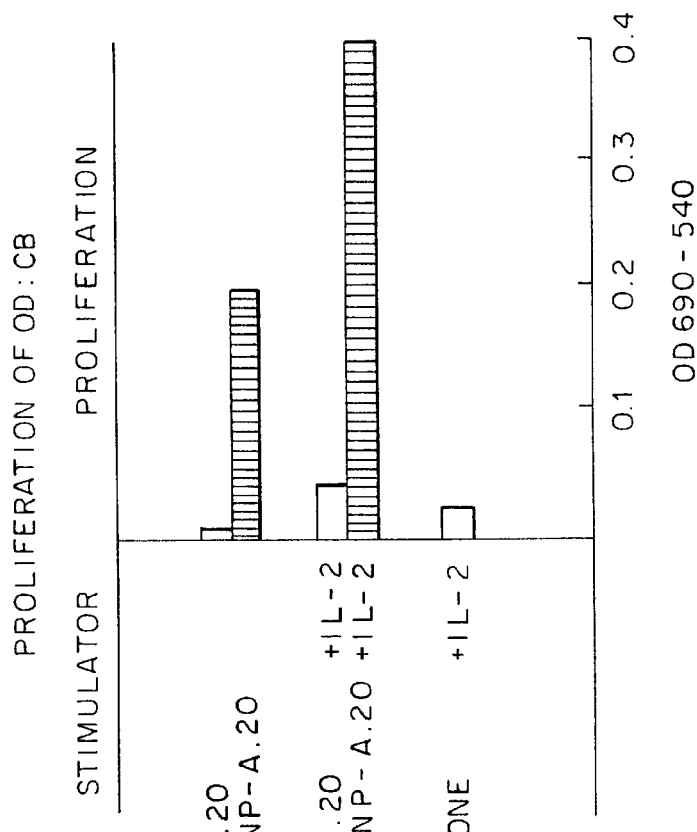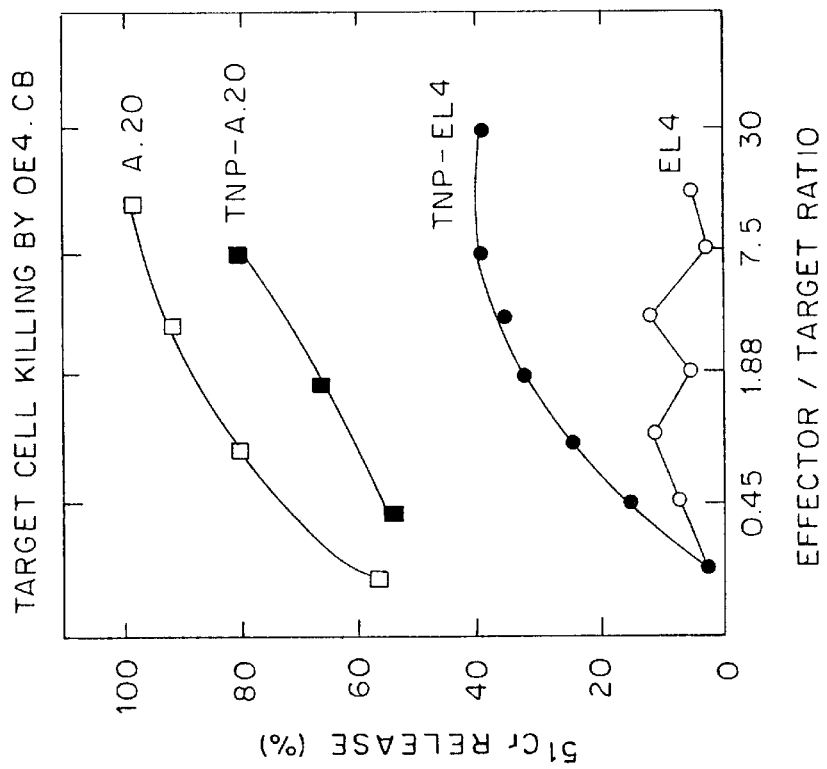
FIG.5B
FIG.5A

FIG. 7 consensus Jk primer:

splice

5' ACTTACGTTTGATCTCCAGGTTGGTCCC 3' consensus JH primer:

splice

5' ACTTACCTGAGGAGACGGTGACCGTGGTCCCTTGGCCCCAG 3' poly (dC) primer:

5' GCGGCCGCCCCCCCCCCCCCCCCCCC 3'

Not I

EXPRESSION-VECTOR CASSETTE FOR CHIMERIC TcR

SYNTHESIZING cDNA WITH REVERSE TRANSCRIPTASE
AND THE COMPLEMENTARY J OLIGONUCLEOTIDE PRIMERS

ADDING A POLY(dG) TAIL AT THE END WITH TERMINAL
DEOXYNUCLEOTIDYL TRANSFERASE (TdT)

USING BOTH J AND POLY (dC) PRIMERS FOR 2nd
STRAND SYNTHESIS AND AMPLIFICATION BY PCR

ENDOWING LYMPHOCYTES WITH ANTIBODY SPECIFICITY

The present application is a continuation of application Ser. No. 07/505,277, filed Apr. 6, 1990, now abandoned, which was a continuation-in-part of application Ser. No. 07/346,483, filed May 2, 1989, now abandoned, the entire contents of both of which are hereby incorporated herein by reference.

FIELD OF THE INVENTION

The present invention relates to gene pairs of recombinant DNA, which gene pairs are adapted to endow mononuclear cells with antibody-type specificity. Various types of cells are suitable, for example, lymphocytes such as T-killer cells, T-helper cells, T-suppressor cells, lymphokine activated cells and any other cell type which expresses the CD3/TcR complex.

The gene pair consists of one gene which comprises a DNA sequence corresponding to exons coding for the constant region of the cell receptor, and another gene which comprises sequences corresponding to the leader and rearranged variable and joining exons encoding a specific antibody's heavy and light chains.

The present invention further relates to suitable vectors for transfecting cells of the type defined above with such gene pairs. The cells may be transfected with a single vector bearing the gene pair, or with two different vectors, each bearing one gene of the gene pairs.

The present invention further relates to cells of the type defined above into which such gene pairs have been introduced so as to obtain their expression, and also to pharmaceutical prophylactic and curative compositions containing an effective quantity of such cells.

In general terms, the present invention relates to a process for the generation of lymphocytes transfected with one or two expression vectors containing DNA encoding a chimeric T-cell receptor. As set out in the following, there was constructed a model system which comprises expression vectors which were transfected and which were functionally expressed in T-killer cells, i.e., which directed the cellular immune response of the lymphocyte against a predefined target antigen in a non-MHC restricted manner.

The recombinant lymphocyte cells of the present invention may be used in new therapeutic treatment processes. For example, T cells isolated from a patient may be transfected with DNA encoding a chimeric receptor including the variable region of an antibody directed toward a specific antigen, and then returned to the patient so that the cellular immune response generated by such cells will be triggered by and directed toward the specific antigen in a non-MHC restricted manner.

Because of the restrictions imposed by corecognition of self MHC plus antigen, the acquisition of new specificity by grafting of TcR genes is limited to inbred combinations. Such manipulations are practically impossible in an outbred population.

BACKGROUND OF THE INVENTION

Unlike antibodies, the T cells recognize antigen only in association with products of the major histocompatibility complex (MHC). Such dual recognition is mediated by combination of the variable regions of both the α and β chains that comprise the antigen recognizing T-cell receptor (TcR). Recently it became possible to endow T cells with a given specificity by DNA mediated transfer of cloned genes coding for the α and β TcR chains (Dembic et al., *Nature*, 320, 232–238 (1986)). In general, the expression as a dimer of both α and β chains of a given TcR has been required in order to display a defined specificity although it has been implicated that the Vβ is responsible for the MHC specificity (Saito et al., *Nature*, 329, 256–259 (1987)).

Expression of a chimeric receptor composed of immunoglobulin-derived V regions and T cell receptor-derived C regions has been achieved by Kuwana et al, *Bioch. Biophys. Res. Comm.*, 149, 960–968 (1987). Expression was achieved in helper T cells and the criterion for expression was an increase in cytosolic calcium concentration. An increase in cytosolic calcium concentration, however, does not establish that one will obtain the various functional activities characteristic of a cellular immune response by helper cells or other lymphocytes.

SUMMARY OF THE INVENTION

In order to overcome the limitations set out above, and in order to be able to design at will T-cells having a desired predetermined specificity, there were constructed T-cells with antibody-type specificity. The invention is applicable to a wide variety of cells as set out herein.

According to the present invention, it is possible to construct and functionally express chimeric TcR that recognize antigen in non-MHC restricted manner, effectively transmit transmembrane signal for T cell activation, and mediate effector cell functions such as lymphokine secretion or killing of target cells.

Based on the extensive degree of similarity in structure and organization between the antibody and TcR molecules, it was assumed that it will be possible to replace the V-region of TcR with an antibody's one in a manner that will result in a chimeric TcR. However, it was not predictable that such chimeric TcR's would retain their T cell functions so as to trigger or direct the cellular immune response of the cell. Even the results of Kuwana et al do not lead to such predictability, particularly in view of the following. First, it is known that there are two signals needed for the activation of T cells (Wagner et al, *J. Exp. Med.*, 155, 1876 (1982)). Kuwana et al disclosed that the receptor expression caused an increase in cytosolic calcium concentration. However, while calcium activation is one pathway leading to T cell activation, there is also another pathway involving inositol phosphate. The rise of calcium alone is inadequate to cause IL-2 production and proliferation of T cells. Although ligand binding to the T cell receptor initiates two early activation signals (calcium raised and PKC activation) as reviewed in Weiss et al, *Ann. Rev. Immunol.*, 4, 543 (1986), they are not sufficient to cause IL-2 production and proliferation of T cells (Linch et al, *Immunolo. Rev.*, 95, 138 (1987)).

Furthermore, killer cells involve different accessory molecules and different target cell presenting antigens compared to helper cells, i.e., MHC Class 1 versus MHC Class 2. Indeed, prior to the present invention it was thought that binding of the receptor to the MHC antigen triggered the lytic action of killer cells; the present inventors discovered that such binding was not necessary in order to trigger killer function. This was certainly not predictable from the work of Kuwana et al.

BRIEF DESCRIPTION OF THE DRAWINGS

FIG. 5 shows TNP specific activity of transfected murine T cell lines. The ability of OE4 cells transfected by cTcR to lyse various target cells was estimated by the $^{51}$Cr killing assay (A). The ability of various stimuli to induce proliferation of OD1 transfected cells was determined by the MTT assay (B).

FIG. 7 shows the oligonucleotides serving as universal consensus primers for $J_H$ and $J_K$.

DETAILED DESCRIPTION OF PREFERRED EMBODIMENTS

Figure 1:
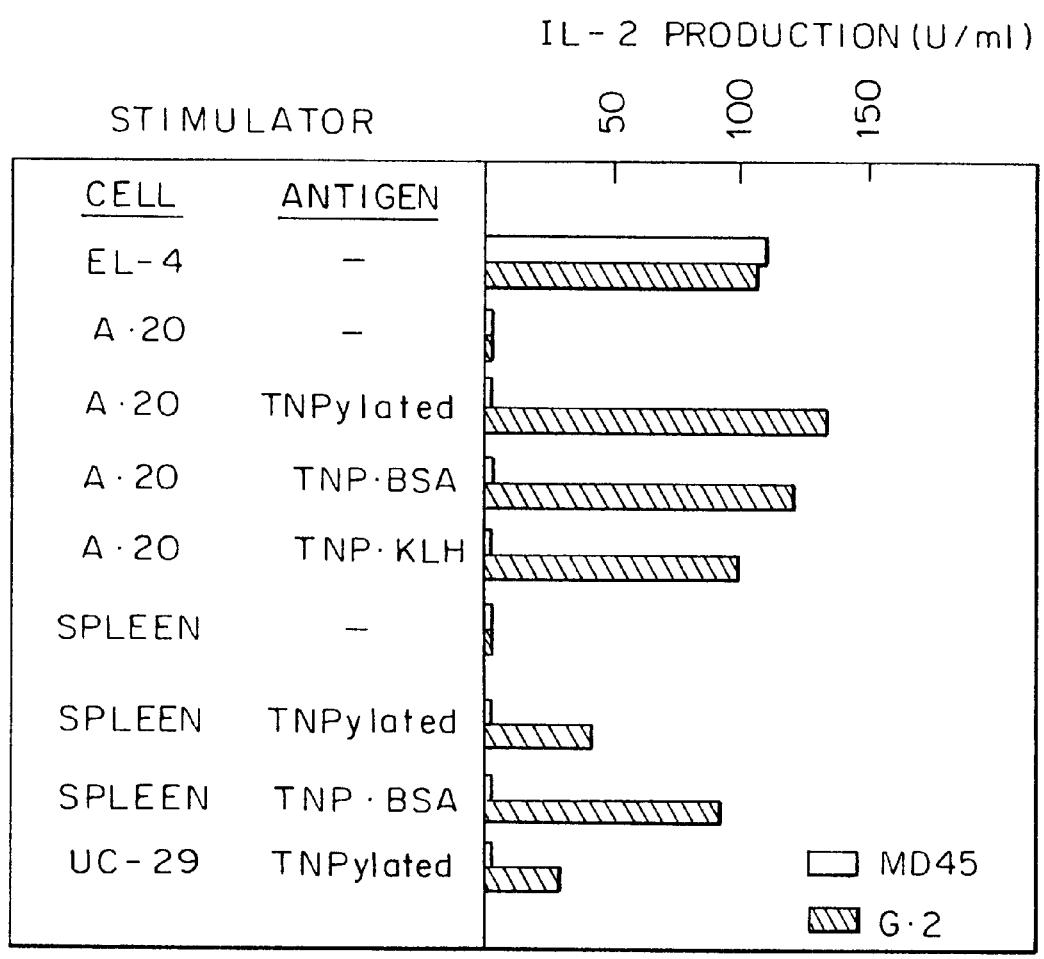
FIG. 1 is a graph showing the degree of IL-2 production by G.2—one of the transfectants which received and express the chimeric TcR (cTcR) genes.

According to the present invention, there were constructed chimeric T cell receptor genes by recombining the $V_H$ and $V_L$ gene segments of an anti-TNP antibody with the constant region exons of the T cell receptor's (TcR) α and β chain. Following transfection into cytotoxic hybridomas, expression of a novel functional T cell receptor was detected. The chimeric receptor manifested the idiotype of the antibody and endowed the T cells with non-MHC restricted, anti-TNP reactivity. This model system demonstrates that chimeric TcR with an antibody-like binding site can be designed and functionally expressed in a variety of T-cells. By means of this manipulation, T-cells of any desired specificity may be engineered at will, provided that such specificity can be predefined by monoclonal antibodies.

The various aspects of the present invention are suitable gene pairs for introduction and expression in certain vectors and the use of such vectors for transfecting cells (T-cells and others, as defined) in order to endow them with a predetermined antigenic specificity. The invention further relates to pharmaceutical compositions for the prevention and cure of certain diseases. Other aspects will become clear hereinafter.

As stated above, the present invention relates to lymphocytes, comprising populations of T-killer cells, T-helper cells, T-suppressor cells, lymphokine activated cells, and any other type of cell which expresses CD3/TcR. As further stated above, the present invention relates to a recombinant gene-pair adapted to endow mononuclear lymphocyte cells with antibody-type specificity, where the genes are:

a. DNA coding for the constant region of a lymphocyte receptor, and preferably genomic segments containing exons coding for the constant region of the T-cell receptor (α, β, γ, δ, chains), and b. DNA coding for the heavy and light chains of an antibody specific for a predefined antigen, preferably gene-segments containing the leader and rearranged variable+joining exons encoding for a specific antibody's heavy and light chains. The mononuclear lymphocyte cells are preferably populations of T-killer cells, T-helper cells, T-suppressor cells, lymphokine activated cells, and the like.

According to a preferred aspect, the present invention relates to a gene pair with gene segments coding for the constant region of α or β chains, each of which being ligated with either the rearranged variable gene segment of the antibody's heavy or light chain, and vice versa. It should be understood that the T-cell receptor from which such constant region is taken can be of the same species or of a different species as the lymphocyte into which it is inserted. Preferably, the rearranged gene segments code for a binding site of an antibody molecule either from the same species of the T-cell receptor gene or another species, where the rearranged gene segments code for antibody specificity towards tumor-specific antigens, tumor-associated antigens, viral antigens, modified self-antigens, parasitic antigens, bacterial antigens, fungal antigens, autoimmune disease type antigens, or other foreign antigens.

According to a further embodiment, the rearranged gene segments code for monoclonal antibodies reacting with a defined type of tumor cells or HIV-infected cells. The invention further relates to expression vectors for the efficient transfection of a cell type, comprising a recombinant gene pair as defined above. Such a vector can be a plasmid or retrovirus backbone containing promoter, polyadenylation site and drug selection markers. Preferred vectors according to the invention are the plasmids pRSV2 and PRSV3. There may be used a pair of expression vectors in which one vector comprises a plasmid with one selection marker (such as neo$^R$) into which a rearranged gene segment coding for the variable region of the antibody's light chain together with either the gene segment coding for the constant region of the T-cell receptors α or β chains are cloned, and the second vector comprises another selection marker (such as gpt) into which a rearranged gene segment coding for the variable region of the antibody's heavy chain together with a gene segment of the constant region of the complementary T-cell receptor's chain (β or α) used in the first vector. Alternatively, DNA corresponding to both chimeric genes, along with a single drug selection marker, may be put on a single vector for transfection into the host cells.

The present invention further relates to mononuclear lymphocyte cells containing a chimeric pair of genes as defined above.

Yet another aspect of the present invention relates to a composition for treating a patient in need thereof comprising as active ingredient lymphocytes which have been taken from the patient, propagated in vitro, and then transfected with a gene pair as above described or with a vector as defined above. Such composition is then re-administered to the patient.

Yet another aspect of the present invention relates to a process for producing expression vectors according to the present invention and for constructing a gene pair which comprises selecting a hybridoma producing a monoclonal antibody for the desired antigen, constructing a genomic or cDNA library from the restricted DNA fragments or RNA that contain the rearranged $V_L$ and $V_H$ exons, isolating the clones carrying full length rearranged $V_L$ and $V_H$ exons, isolating from them the DNA segments containing the leader exon and the rearranged $VDJ_H$ and $VJ_L$ exons and subcloning each of them into an expression vector containing either the $neo^R$ or gpt selection marker, inserting into each of the same vectors, 3' to the $VDJ_H$ or $VJ_L$, either one of the genomic or cDNA fragments containing all of the constant region exons and 5' flanking untranslated regions of the T-cell receptor α, β, γ or δ chains isolated from embryonic DNA or cDNA library, resulting in a set of chimeric genes comprised of $V_H C\alpha$, $V_L C\beta$, $V_L C\alpha$, $V_H C\beta$, $V_H C\gamma$, $V_L C\gamma$, $V_H C\delta$, $V_L C\delta$, each of which is cloned in one of the expression vectors containing either the $neo^R$ or gpt selection markers.

Another aspect of the present invention is, in the process of joining a vector (e.g., plasmid or retroviral) to DNA sequences coding for an antibody variable region and to DNA sequences coding for the constant region of a T cell receptor, the improvement wherein the polymerase chain reaction is used to amplify mRNA sequences coding for the variable region into DNA sequences coding for the variable region.

A key element in this innovation is the construction of chimeric Ab/TcR genes. Until recently it involved cloning of the genes encoding the heavy (H) and light (L) chains of the antibody, isolation of the gene segments encoding the rearranged $VDJ_H$ and $VJ_L$, splicing them to the TcR's Cα and Cβ genes and cloning the chimeric genes into vectors that allow their expression in T cells. These procedures are lengthy and require special conditions for each antibody.

We have recently developed a modified protocol that enables the generalization of the procedures to any antibody, and facilitates, quickens and simplifies the genetic engineering manipulations involved in the construction of the cTcR genes. Practically, these modifications are based on two major techniques we have recently developed.

1) Amplification of rearranged $V_H$ and $V_L$ genes directly from mRNA of any antibody forming cell, using the polymerase chain reaction (PCR) and primers composed of consensus sequences of $J_H$ and $J_L$ for the 3' end and poly (dG) tail for the 5' end.

2) Cloning of the amplified ($V_H$ and $V_L$) genes directly into expression vectors, containing the Cα and Cβ of the TcR.

1) Cloning of $V_H$ and $V_L$ by PCR

Oligonucleotide primers are used (FIG. 7) that correspond to the 3' ends of the joining (J) gene segment of the immunoglobulin H and L chain with a 3' donor splice signal (FIG. 7). The sequences of these primers were adopted according to (11) to fit consensus sequences common to all murine $J_H$ and $J_L$ and the splice sequence was added to allow splicing to the first exon of the genomic TcR constant region. mRNA is prepared from the antibody forming cells (hybridomas or B cells) and a cDNA strand is generated, using reverse transcriptase and one of the primers. A short poly (dG) tail is added, 5' to this strand, using the enzyme terminal deoxynucleotydyl transferase. An oligo (dC) primer that contains a rare restriction site (Not I, FIG. 7) is now added as the second primer and the PCR is carried on to amplify the gene segment between the two primers (12,13). The PCR product can be directly cloned into the expression cassette described below. The rare restriction site assists to choose clones with the right orientation.

2) Expression cassette for cTcR

Figure 8:
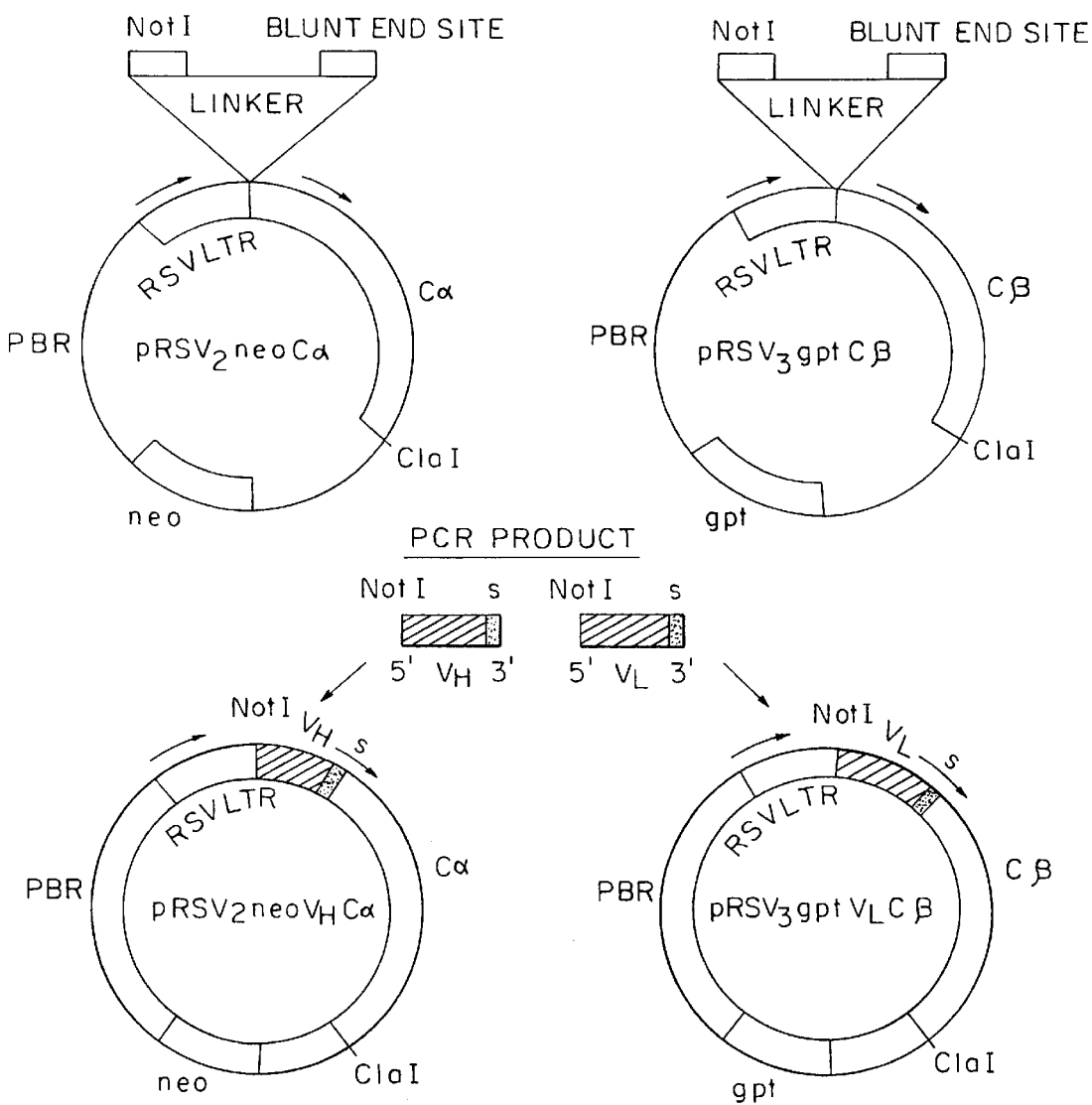
FIG. 8 shows the shuttle cassette vectors used to express the chimeric-TcR genes.

The basic components of the expression cassette are the vectors pRSV2neo and pRSV3gpt (FIG. 8), which we have described before (3) that contain genes that allow for selection against neomycin (G418) and mycophenolic acid, respectively, eukaryotic transcription control elements derived from the long terminal repeat (LTR) of Rous sarcoma virus, and a unique BamHI cloning site. Into this site were cloned genomic BamHI fragments containing the constant region genes of either TcR α or β chain in the right transcriptional orientation. The 3' resulting BamHI site was converted, by partial BamHI digestion following by Klenow treatment, into a unique ClaI site that can be used for either linearization of final constructs, or cloning another gene of interest. The 5' BamHI site is used for cloning the amplified $V_H$ or $V_L$ genes described above.

FIG. 9 describes schematically the procedure in which we use the PCR to amplify mRNA from hybridoma producing anti-IgE mAbs, using $V_H$ and $V_L$ primers for reverse transcriptase cDNA synthesis. Following separation of the cDNA using spermin, oligo (dG) tail was added, using terminal deoxynucleotydyl transferase and PCR amplification was carried out using oligo (dC) as a 5' end primer. The products of this reaction are described in FIG. 10. The 0.5 Kb band in lane 2 represents the $V_H$ fragment and the 0.5 Kb band in lane 3 represents $V_L$ gene segment. The upper part shows the EtBr stained gel, the middle and lower parts of FIG. 10 describe Southern analysis, using $^{32}P$-$V_H$ probe and $^{32}P$-$V_L$ probe correspondingly.

One aspect of the present invention relates to a process where a combination of two plasmids is used for the transfection of the T-cell, one of which comprises the variable of the light chain with either the constant region of α or β; the other the variable of the heavy chain with either of the Cα or Cβ. In another aspect, both regions are present in the same plasmid or other vector.

The following is a description of a model experiment which demonstrates the feasibility of the above general principles and its wide scope of applicability. The invention is not restricted to this specific embodiment.

To construct the chimeric TcR genes we ligated genomic segments each one containing the rearranged VJ and leader exons of either heavy or light chain of the Sp6 anti-TNP, IgM antibody (Ochi et al., Proc.Natl.Acad.Sci.USA, 80, 6351–6355 (1983)) with constant region exons of either the α or β chains of the TcR. The chimeric genes were inserted into pRSV based expression vectors containing the Rous sarcoma promotor and either the $neo^R$ or the gpt drug resistance genes. By protoplast fusion each of the vectors were transfected into MD.45—a CTL hybridoma of BALB/c origin that can be stimulated by H-$2D^b$ cells both for IL-2 production and specific killing of target cells (Kaufmann et al., Proc.Natl.Acad.Sci.USA, 78, 2502–2507 (1981)). Out of the drug resistant transfectants, cells were selected that transcribed the chimeric gene (using $V_H$ and $V_L$ probes). The clone producing the highest levels of one chain, was retransfected with the construct containing the complementary chain and the other drug marker. Double transfectants that grew in the presence of both mycophenolic acid and G.418 were checked by Northern analysis for the transcription of both chimeric genes and by immunoblotting and immunoprecipitation for the expression of the Sp6 idiotype (using the 20.5 mAb). The functional expression of the chimeric receptor was evaluated by the ability of the cells to respond by IL-2 production to TNPylated cells of various origins and by TNP-protein antigens either alone or presented by different cells.

Figure 2:
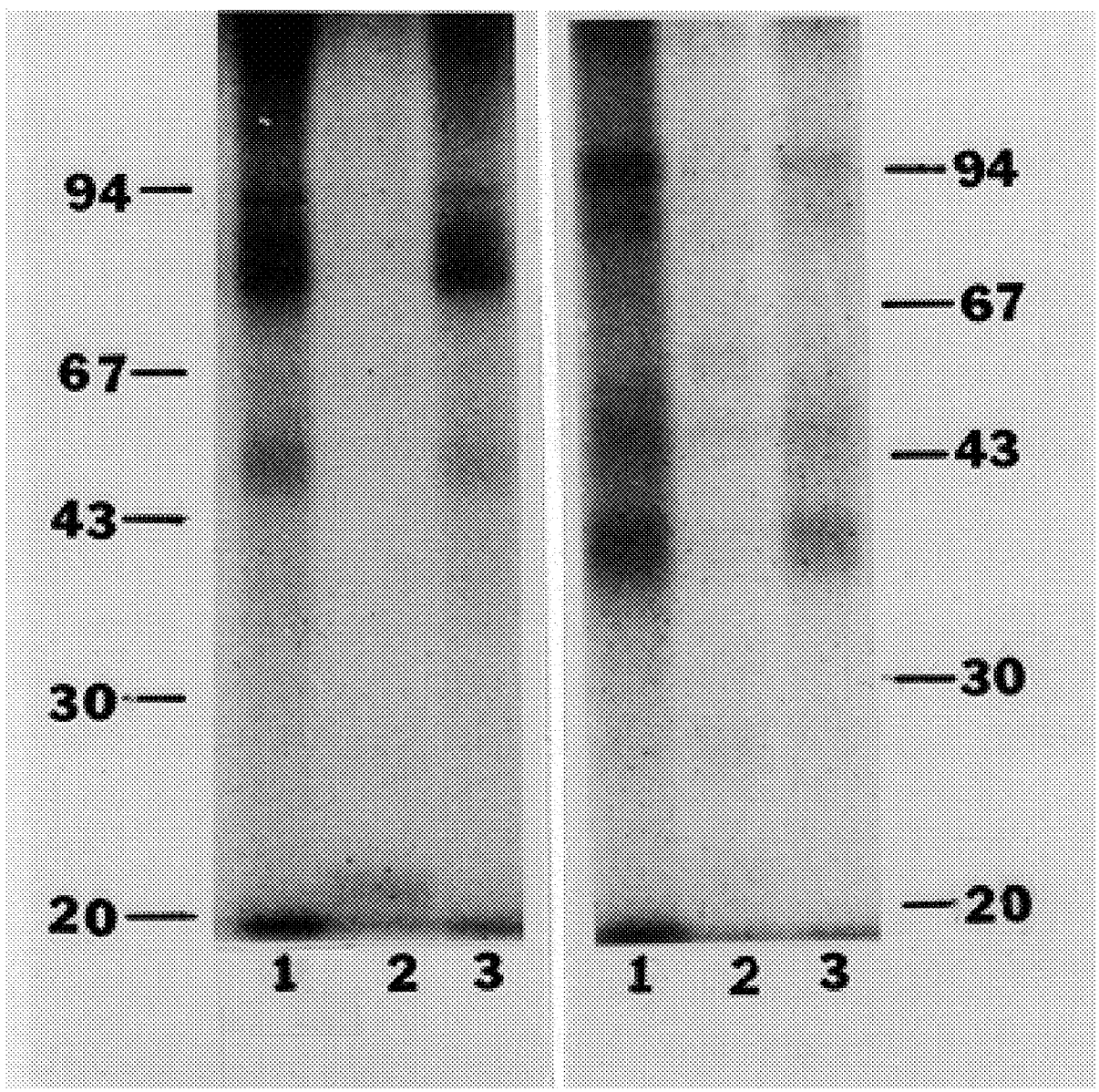
FIG. 2 shows the analysis of the expression of chimeric polypeptide analyzed by immunoblotting of cell lysates and by immunoprecipitation.

Following DNA transfer of the chimeric genes combination of either $V_LC\alpha+V_HC\beta$ or $V_LC\beta+V_HC\alpha$ into the MD.45 CTL hybridoma, almost all the transfectants transcribed both complementary chains of 1.8 Kb for $V_LC\alpha$ or $\beta$ and 1.9 Kb for $V_HC\alpha$ and $\beta$ chains (Gross et al., Proc.Natl.Acad.Sci.USA, 86, 10024 (1989)). The expression of the chimeric polypeptide was analyzed by immunoblotting of cell lysates using anti-Sp6 idiotype mAb 20.5 or by immunoprecipitation using the 20.5 mAb and anti-TcR β8.3 subgroup F23.1 mAb (FIG. 2). Under non-reducing conditions the anti-id and antiβ TcR reacted with a broad band of apparent molecular weight of 80 Kd that is composed of two bands of 83 Kd and 77 Kd. In some transfectants a band of 42–45 Kd was also apparent. After reduction, however, the idiotypic determinant recognized by 20.5 mAb in the immunoblot was destroyed and the 80 Kd complex was dissociated into the 42 Kd polypeptide. Interestingly, transfectants that received either the $V_HC\alpha$ or $V_HC\beta$ alone also expressed the 83 Kd complex as well as the 42 Kd chain carrying the 20.5 idiotype. Considering that Md.45 hybridoma expresses its αβ dimer (Becker et al., Nature, 316, 606–619 (1985)) and only the β chain of BW 5147 fusion partner (Lustgarten and Eshhar, unpublished data), together with the fact that the 20.5 idiotype (as well as the anti-TNP binding site) is expressed solely on $V_H$ Sp6, we can conclude that in transfectants that had received the $V_HC\alpha$ or $V_HC\beta$ gene, a chimeric chain is expressed that can form functional dimer with the autologous complementary α or β TcR chains. The chains in part of the dimers are not linked by disulfide bond and therefore migrate as single chain in SDS-PAGE. The double transfectants most likely express on their surface in addition to the $V_LC\alpha$–$V_HC\beta$ (or $V_LC\beta$–$V_HC\alpha$) chimeric receptor dimers, also the heterodimers that result from various combinations of pairing of the chimeric chain with the complementary endogenous α and β chains. These result in the broad band observed in the immunoprecipitation of surface iodinated TcR by either anti-id or anti-TcR (FIG. 2).

In order to study whether the chimeric receptor preserved the antibody's anti-TNP specificity and the ability to transmit transmembrane signal for T cell activation, we coincubated the transfectants with different stimulator cells either TNPylated or in the presence of various TNP-protein antigens. FIG. 1 shows the degree of IL-2 production by G.2—one of the transfectant that received $V_LC\beta+V_HC\alpha$ chimeric genes. The transfected cells expressed on their surface both the endogenous TcR as evidenced by their reactivity (like the parental MD.45 hybridoma) toward EL-4 stimulator cells. Unlike MD.45, they underwent triggering by TNP covalently coupled to A.20 (BALB/c B lymphoma) or UC.29 (human B lymphoblastoid) and other TNP modified cells. In addition TNPylated proteins (such as TNP-BSA, TNP-KLH and others), could stimulate IL-2 production by G.2 either when immobilized on plastic and even better in the presence of BALB/c spleen cells or A.20 cells that are known to be good antigen presenters. Interestingly, the transfectants that received only the $V_HC\alpha$ or the $V_HC\beta$ chimeric gene and expressed the Sp6 idiotype, could also respond to TNP indicating that the $V_H$ of Sp6 contains all the information needed to construct the TNP-binding site.

Another manifestation of the functional expression of the chimeric receptor in the effector phase of T-cell response was demonstrated by the ability of the transfectants to specifically kill haptenated target cells as measured by the $^{51}$Cr-release assay.

For one set of $^{51}$Cr-release assay experiments, in the first round of transfections with single chimeric genes, out of 48 cells seeded for each transfection, growth was seen in 21 of those that received $V_LC\alpha$ (termed GTA.a), 15 that received $V_LC\beta$ (termed GTA.b), 9 that received $V_HC\alpha$ (termed GTA.c), and 13 that received $V_HC\beta$ (termed GTA.d). Clones expressing high RNA levels of each series were then transfected with the complementary construct. In all, out of $3\times10^7$ cells transfected, 54 independent transfectants were obtained from GTA.a that received the $V_HC\beta$ construct (termed GTA.e), 13 from GTA.b that received $V_HC\alpha$ (termed GTA.f), 10 from GTA.c that received $V_LC\beta$ (termed GTA.g), and 18 from GTA.d that received $V_LC\alpha$ (termed GTA.h).

Figure 3:
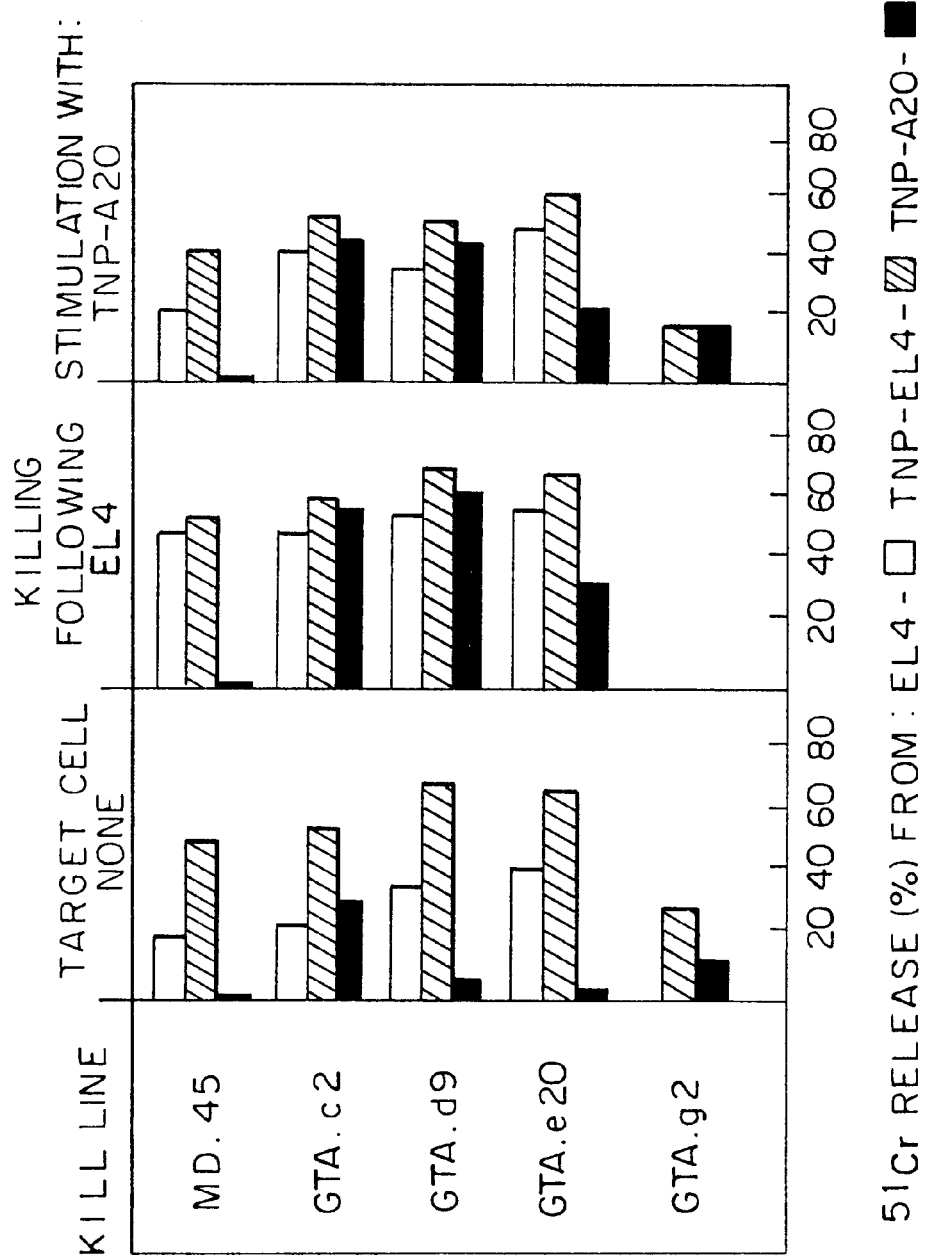
FIG. 3 shows cytotoxic activity of transfectants. The different transfectants and MD.45 parental cells were incubated at an effector:target ratio of 2:1 with $^{51}$Cr-labeled target cells. Effector cells were used either without stimulation or following preincubation with irradiated EL4 or TNP-A.20 stimulator cells.

In the $^{51}$Cr-release assay (9), target cells were modified by TNP using 10 mM 2,4,6-trinitrobenzenesulfonic acid as described (10). Killing assays were performed at different ratios of effector to $^{51}$Cr-labeled target cells for 4–8 hr. As shown in FIG. 3, all cells studied (except GTA.g2, which lost its ability to recognize EL-4 cells) killed EL-4 (the H-$2^b$ target cell of the MD.45 hybridoma) as well as TNP-EL4 cells and their lytic ability was increased following pre-stimulation with EL-4. However, only the transfectants could kill the TNP-A.20 target cells. Accordingly, stimulation with TNP-A.20 cells enhanced only the cytolytic reactivity of cells that expressed the chimeric TcR. Similar results have been obtained when TNP-458,H-$2^S$ B-lymphoma cells were used as targets in the killing assay. These studies are compatible with the idea that the chimeric receptor can mediate non-MHC restricted, antigen-specific target cell lysis.

We attempted to transfect the $V_HC\alpha+V_LC\beta$ chimeric genes encoding for the Sp6 anti-TNP variable region into various T cell clones and tumor lines. The following T cells were used for transfection: OE4 is an anti-H-$2^d$ allospecific cytotoxic T cell line (4). OD1 is an ovalbumin specific, I-A$^d$ restricted helper T cell line (5). Jurkat is a CD4$^+$ human T cell tumor. As target cells served: A.20, a BALB/c B cell line; NSO, a BALB/c myeloma/; RBL, a rat basophil leukemia cell/; and K562, a human myeloid cell line. pRSV2neo$V_HC\alpha$ and pRSV3gpt$V_LC\beta$ (3) were linearized by cleavage at a unique restriction site in the non-coding region of the vectors. About 20 μg DNA were used to transfect $20\times10^6$ cells either by electroporation (6) or lipofectin (7). Following transfection, cells were allowed to recover in non-selective culture medium. Conditioned medium and specific antigen presenting cells were added to the murine cell lines. After recovery of the cultured cells, selective drugs (G418 or mycophenolic acid) were added in the minimal concentrations that were found to inhibit the growth of non-transfected cells. Following 4–5 weeks of selection, growing cells were cloned and sub-cloned by limiting dilutions.

Figure 4:
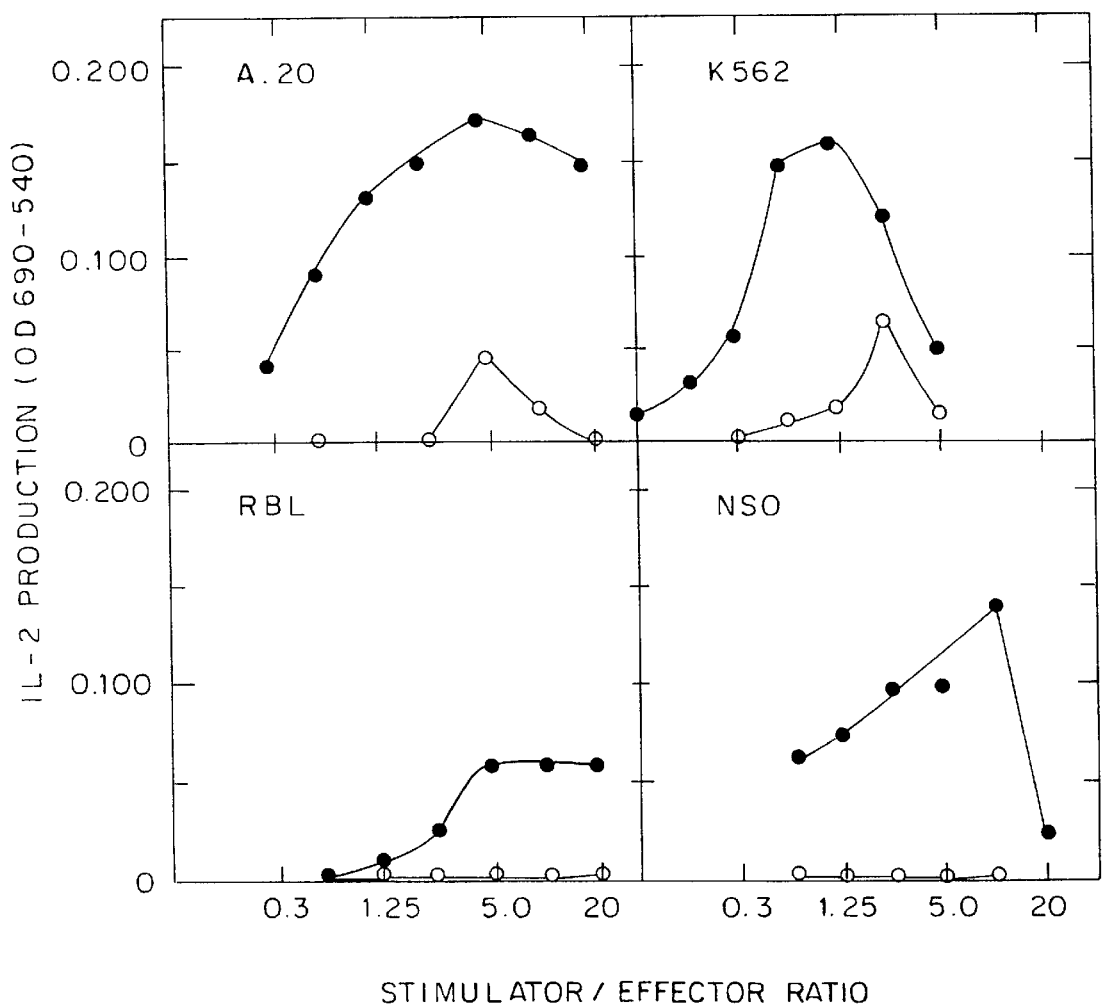
FIG. 4 shows stimulation of Jurkat cells expressing the chimeric-TcR by TNP-modified (closed circle) or non-modified (open circle) cells. IL-2 production following 24 hr stimulation was determined by the proliferation of CTL-L cell line using the MTT calorimetric assay.

In the first set of experiments, we transfected the Jurkat human T cell line by electroporation. Following transfection the cells were distributed at a concentration of $10^5$/ml/cell in regular growth medium. 48 hours later, G418 and mycophenolic acid were added. Cell growth was apparent in about 60% of the wells, 2–3 weeks after transfection in the presence of selective medium. More than half of the transfectants transcribed the $V_HC\alpha$ and could be stimulated by TNP-A.20 cells to yield IL-2. However, the most active transfectants, exemplified by clone JCB6 (FIG. 4) which transcribed both chimeric chains. As shown in FIG. 4 this transfectant could undergo stimulation by TNP-modified cells of different origin (human-K562, rat-RBL or mouse-A.20 and NSO). Non-TNPylated cells failed to trigger any response. Transfectants that expressed $V_LC\beta$ alone did not display TNP specificity. As for the MD.45 hybridoma, the human Jurkat cells expressing both chimeric genes, displayed on their surface sufficient amounts of cTcR which could be detected either by the anti-Sp6 idiotypic mAb 20.5 and by the anti-murine TcR mAb H.57. These studies indicate that cTcR genes, even of murine origin, can associate with the human CD3 complex and be expressed as functional receptors in human cells.

For practical application it is more crucial to study the expression of the chimeric receptor in T cell lines. Such cells are dependent for their replication on T cell growth factors, and are more susceptible than tumor cells or hybridomas. Indeed, the frequency of drug resistant transfectants which we obtained after transfecting either the OE4 cytotoxic murine T cell clone or the OD1 helper T cell clone was very low. In fact, using either electroporation or the less traumatic lipofectin mediated transfection, we got only few drug resistant OE4 cells and practically none of the OD1. We therefore have changed our selection strategy by omitting the selective drugs and at different time intervals following transfection, removed IL-2 from the growth medium and replaced it with specific stimulus in the form of TNPylated target cells. In preliminary experiments we could indeed induce TNP-specific proliferation of transfected cells. As can be seen in FIG. 5B, OD1 cells following transfection with the anti-TNP $V_H C\alpha + V_L C\beta$ chimeric genes (OD1.CB) could proliferate in the presence of TNP-A.20. As expected, the addition of external IL-2 enhanced this TNP-specific proliferation. Non-TNPylated A.20 cells have no effect, and in the 24 hr assay period, IL-2 alone has only marginal effect. The cTcR genes conferred TNP specificity also on the cytotoxic OE4 cell line. OE4 is of C57BL/6 origin and kills specifically H-$2^d$ target cells, such as A.20 (FIG. 5A). However, as shown in the figure, OE4.CB that was co-transfected and selected for growth in the presence of both selective drugs, could kill TNP-EL4 (H-$2^b$) and not EL4 cells. Untransfected OE4 cells failed to kill TNP-EL4 or EL4 cells. These are experiments in which we could demonstrate the expression of the cTcR by functional assays. The yield of functional transfectants in the experiments described above was low. We recognize the transfection method as the most critical stage in determining the yield and level of expression of the cTcR genes. Transduction of genes with retroviral vectors have been proved recently quite an effective method for DNA mediated gene transfer into human T cells (8).

In order to further establish the generality of the cTcR approach and to construct and express cTcR made of binding sites of anti-tumor antibodies in a functional manner, we have chosen two systems. The first was comprised of the murine B cell lymphoma 38C13 that express surface IgM. The idiotype of such IgM can serve as unique tumor cell antigen and we used the SIC5 anti-38C13 id mAb (Moloney, D. G. et al., *Hybridoma*, 4, 191, 1985), as the model to construct anti-tumor specific cTcR. The second system was comprised of the monoclonal antibody OVB3 (Willingham, M. C. et al., *Proc.Natl.Acad.Sci.(USA)*, 84, 2474, 1987) specific to the OVCAR, a human ovarian cell carcinoma which grows in tissue culture or as a tumor in nude mice.

Chimeric TcR genes were prepared from cloned $V_H$ and $V_L$ genes of the SIC5 and OVB3 mAbs basically as described herein or as detailed in Gross, Waks and Eshhar, *Proc.Natl.Acad.Sci.(USA)*, 86, 10024 (1989), the entire contents of which are hereby incorporated by reference. For transfection we used the cytotoxic T cell hybridoma MD45 or a TcR deficient mutant (27J) which we isolated from the MD45 hybridoma.

As shown in Table I, demonstrating the activity of a transfectant receiving the SIC5-based cTcR genes, the cTcR conferred on the transfected T cell hybridoma specificity against the 38C13 lymphoma tumor target cell. The transfectant underwent stimulation for IL-2 secretion by 38C13 cells or 38C13 IgM when immobilized to plastic. The specificity, like that of the parental SIC5 mAb, was directed at the 38C13 idiotype; hence, the mutant that lost the idiotype failed to stimulate. Therefore, as we showed before in the anti-TNP system, the cTcR conferred on the cells non-MHC restricted antibody type specificity. Again, stimulation through the cTcR triggered the T cell hybridoma to its full activity.

Figure 6:
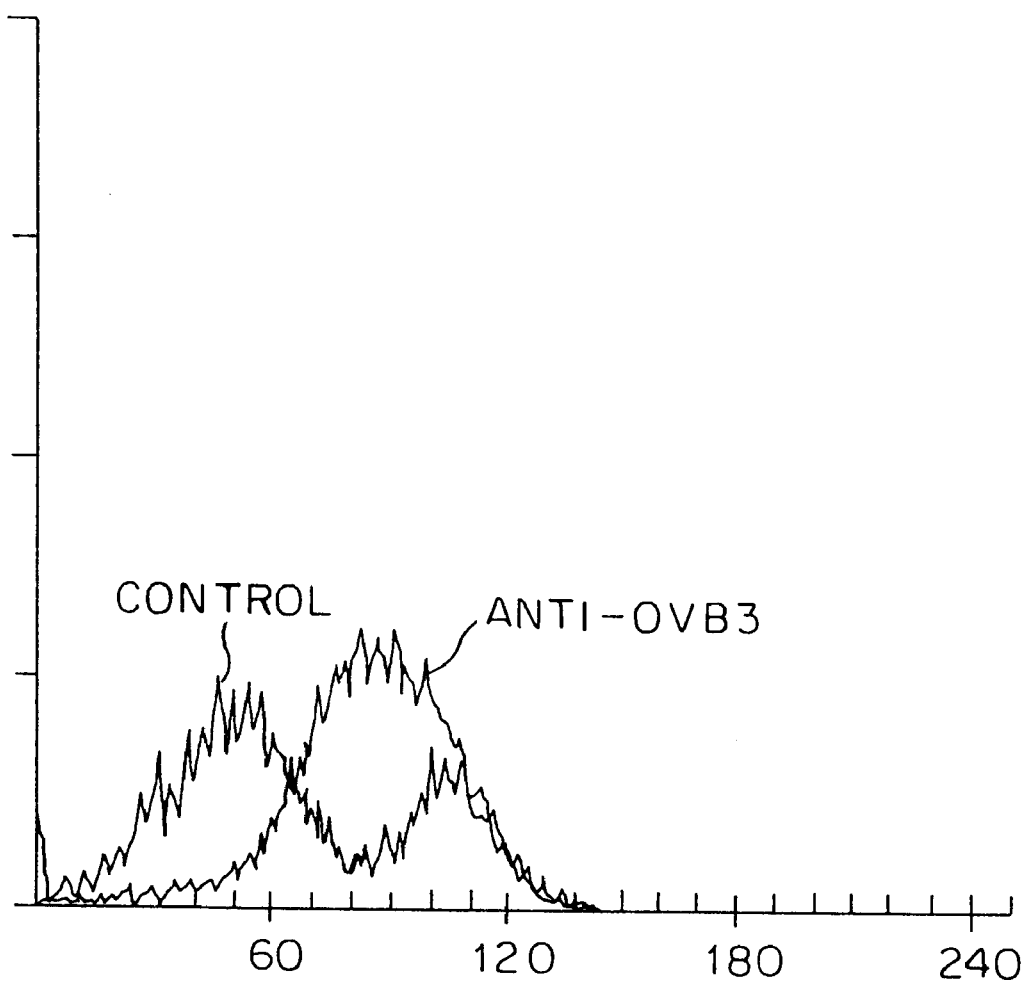
FIG. 6 shows expression of cTcR directed at human ovarian cell carcinoma on the surface of T cells transfected with the OVB3-cTcR. Immunofluorescence staining was performed using purified polyclonal rabbit anti-OVB3 mABs, and analyzed by the FACS IV. Control staining gave 2 peaks the first negative, the second due to Fc receptor bearing T cells.

In the OVB3 anti-human ovarian carcinoma cell system we could show that T cell transfectants that received the OVB3-cTcR genes expressed on their surface the OVB3 idiotype (FIG. 6). These transfectants could be also stimulated by the OVCAR tumor cells (not shown).

TABLE I

Activity of T cells transfected with chimeric TcR genes composed of antibody binding site specific to lymphoma surface idiotypes[a].

| Experiment | Stimulation | E/T | IL-2 Production |
|---|---|---|---|
| I | 38C13 cells | 2:1 | 0.290 |
|  |  | 9:1 | 0.300 |
|  |  | 1:5 | 0.280 |
|  | Id-mutant | 1:1 | 0.025 |
| II | Plastic Bound 38C13 IgM | Soluble 38C13 (µg/ml) | IL-2 Production |
|  | − | — | 0.010 |
|  | + | — | 0.245 |
|  | + | 50 | 0.001 |
|  | + | 5 | 0.015 |
|  | + | 0.5 | 0.152 |
|  | + | 0.005 | 0.235 |

[a]CTL hybridoma, lacking the TcR chain were cotransfected with cTcR genes composed of $V_H$ and $V_L$ of mAb SIC5 (anti-38C13 id). Following selections for growth in G418 and mycophenolic acid, transfectants were analyzed for their ability to undergo stimulation with the 38C13 lymphoma cells (Exp. 1) or plastic bound 38C13 IgM (Exp.II). Soluble 38C13 IgM at various concentrations served as specific inhibitor in the secondexperiment. As controls in both experiments, we used either the cells or IgM of 38C13 mutant that does not bind the SIC5 mAb. In both experiments stimulation was evaluated for 24 hr. The amount of IL-2 produced following stimulation was evaluated by its ability to support the growth of CTLL line as measured by the MTT assay Taken together, our results clearly demonstrate that it is possible to construct, transfect and functionally express chimeric T cell genes that manifest antibody specificity. This novel approach should be extended to enable the engineering at will of the specificity of T cells in non-MHC restricted manner, in a way that a given set of genes could be transferred to T cells of any origin. Such T cells could then be returned to their donor and manifest the acquired specificity. Following such manipulation, the cells acquire a new specificity encoded by the chimeric genes that is of antibody-type, i.e., not restricted by self-MHC molecules.

The results obtained demonstrate that in a similar manner it is possible to prepare a wide variety of pairs of such chimeric genes that are directed at various target antigens which are predefined by specific monoclonal antibodies. Such antigens can be those found in tumor cells of a certain cancer, viral antigens, modified self antigens, antigens of bacteria, parasites, fungi, antigens of autoimmune diseases, and any other antigens toward which directing cellular immune responses can benefit the patient. It is one of the advantages of this invention that it enables taking the patient's own cells, their propagation in vitro, to select (if needed) a certain effector subpopulation (killers, helper, or suppressor cells), and to direct the desired specificity of such cells by introducing into them the pair of engineered chimeric genes. Such cells, upon reimplantation into the patient, will function against the target antigens as dictated by the chimeric genes.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

REFERENCES

1. Gross G, Waks T, Eshhar Z (1989). Functional expression of a chimeric T cell receptor with an antibody binding site. In Kaplan J G, Green D R, Bleakley R C (eds) "Cellular Basis of Immune Modulation", New York: Alan R. Liss, p. 97.

2. Gross G, Gorochov G, Waks T, Eshhar Z (1989). Generation of effector T cells expressing chimeric T cell receptor with antibody type specificity. *TransP Proc* 21:127.

3. Gross G, Waks T, Eshhar Z (1989). Expression of immunoglobulin/T cell chimeric molecules as functional receptors with antibody-type specificity. *Proc.Natl.Acad.Sci. (USA)* 86:10024.

4. Staerz U D, Kanagawa O, Beran M (1985). Hybrid antibodies can target sites for attack by T cells. *Nature* 314:628.

5. Puri J, Lonai P, Friedman Y (1986). Antigen-IA interaction and the proteolytic processing of antigen: The structure of the antigen determines its restriction to the A or E molecule of the MHC. *Eur J Immunol* 16:1093.

6. Fotter H, Weir L, Leder P (1984). Enhancer dependent expression of human x immunoglobulin genes introduced into mouse pre B lymphocytes by electroporation. *Proc.Natl.Acad.Sci.(USA)* 81:7161.

7. Felgner P L, Gradek T R et al (1987). Lipofectin: A highly efficient, lipid mediated DNA transfection procedure. *Proc.Natl.Acad.Sci.(USA)* 84:7413.

8. Kasid A, Morecki S et al (1990). Human gene transfer: Characterization of human tumor-infiltrating lymphocytes as vehicles for retroviral-mediated gene transfer in man. *Proc.Natl.Acad.Sci.(USA)* 87:473.

9. Kaufmann, Y., Berke, G. & Eshhar, Z. (1981) *Proc.Natl.Acad.Sci.(USA)*, 78, 2502–2506.

10. Schmidt, A. M., Pettinelli, C. B., Henkart, F. A., Lunney, J. K. & Shearer, G. M. (1978) *J. Exp. Med.* 147, 352–368.

11. Orlandi R, Gussow D H, Jones P T and Winter G (1989). Cloning immunoglobulin variable domains for expression by the polymerase chain reaction. *Proc.Natl.Acad.Sci.(USA)*, 86, 3833–3837.

12. Bell (1989). The polymerase chain reaction. *Immunol Today*, 10, 351–355.

13. Mulis K B and Faloon F A (1987). Specific synthesis of DNA in vitro via a polymerase-catalysed chain reaction. *Method Enzymol*, 155, 335–350.

We claim:

1. A mononuclear T-killer cell which expresses a chimeric receptor which permits said cell to selectively kill target cells bearing a predefined target antigen in a non-MHC restricted manner, said cell containing recombinant DNA encoding said chimeric receptor, said DNA comprising:

a. DNA coding for the two chains of the constant region of a T-cell receptor (TcR), said two chains being the α and β chains or the γ and δ chains, and b. DNA coding for the variable regions of the heavy and light chains of an antibody specific for the predefined target antigen, such that, when expressed, one of said heavy and light chains of said antibodies is attached to one of said two chains of said T-cell constant region and the other of said heavy and light chains of said antibodies is attached to the other of said two chains of said T-cell constant regions.

2. A mononuclear T-killer cell according to claim 1, wherein the cell into which said DNA is inserted is taken from a patient who is to be treated with the modified T-killer cells.

3. A pharmaceutical composition for treating a patient in need thereof comprising as active ingredient an effective quantity of mononuclear T-killer cells in accordance with claim 1, and a suitable carrier or adjuvant.

4. A pharmaceutical composition in accordance with claim 3, wherein the cell into which said DNA is inserted is taken from a patient who is to be treated with the modified T-killer cells.

5. A mononuclear T-killer cell in accordance with claim 1 that is a human cell.

6. A mononuclear T-killer cell in accordance with claim 1, wherein:

(a) said DNA coding for the two chains of the constant region of a TcR are genomic segments containing exons for said two chains; and (b) said DNA coding for the variable regions of the heavy and light chains of an antibody specific for the predefined target antigen are gene-segments containing the VDJ region leader, variable, and joining exons encoded in said antibody's heavy and light chains.

7. A mononuclear T-killer cell in accordance with claim 6, wherein said genomic segment (a) codes for the constant region of TcR α and β chains.

8. A mononuclear T-killer cell in accordance with claim 1, wherein the TcR and the antibody from which said DNA of (a) and (b), respectively, is obtained are of the same species.

9. A mononuclear T-killer cell in accordance with claim 1, wherein the TcR and the antibody from which said DNA of (a) and (b), respectively, is obtained are of different species.

10. A mononuclear T-killer cell in accordance with claim 1, wherein said heavy and light chains are from an antibody specific towards a tumor-specific antigen, a tumor-associated antigen, a viral antigen, a modified-self antigen, a parasitic antigen, a bacterial antigen, a fungal antigen or an autoimmune disease type antigen.

11. A mononuclear T-killer cell in accordance with claim 10, wherein said antibody is a monoclonal antibody reacting with a defined type of tumor cell.

12. A mononuclear lymphocyte cell which expresses a chimeric receptor which permits said cell to direct its cellular immune response toward a predefined target antigen in a non-MHC restricted manner, said cell containing recombinant DNA encoding said chimeric receptor, said DNA comprising:

a. DNA coding for an α, β, γ or δ chain of the constant region of a T-cell receptor (TcR), and b. DNA coding for the $V_H$ region of an antibody specific for the predefined target antigen, wherein said antibody is specific towards a tumor specific antigen, a tumor associated antigen, a viral antigen, or an autoimmune disease type antigen.

13. A mononuclear lymphocyte cell in accordance with claim 12, wherein said DNA coding for an α, β, γ or δ chain of the constant region of a TcR is DNA coding for an α chain thereof.

14. A mononuclear T-killer cell in accordance with claim 12, wherein said DNA coding for an α, β, γ or δ chain of the constant region of a TcR is DNA coding for an β chain thereof.

15. A mononuclear T-killer cell in accordance with claim 12, wherein the TcR and the antibody from which said DNA of (a) and (b), respectively, is obtained are of the same species.

16. A mononuclear T-killer cell in accordance with claim 12, wherein the TcR and the antibody from which said DNA of (a) and (b), respectively, is obtained are of different species.

17. A mononuclear T-killer cell in accordance with claim 16, wherein said antibody is a monoclonal antibody reacting with a defined type of tumor cell.

18. A mononuclear T-killer cell according to claim 12, wherein the cell into which said DNA is inserted is taken from a patient who is to be treated with the modified lymphocytes.

19. A pharmaceutical composition for treating a patient in need thereof comprising as active ingredient an effective quantity of mononuclear lymphocyte cells in accordance with claim 12, and a suitable carrier or adjuvant.

20. A pharmaceutical composition in accordance with claim 19, wherein the cell into which said DNA is inserted is taken from a patient who is to be treated with the modified lymphocyte cells.

21. A mononuclear lymphocyte cell in accordance with claim 12 that is a human cell.

22. A mononuclear lymphocyte cell in accordance with claim 12 that is a T-killer cell, wherein said chimeric receptor permits said cell to selectively kill such target cells in a non-MHC restricted manner.

23. A mononuclear lymphocyte cell which expresses a chimeric receptor which permits said cell to direct its cellular immune response toward a predefined target antigen in a non-MHC restricted manner, said cell containing recombinant DNA encoding said chimeric receptor, said DNA comprising:
   a. DNA coding for the two chains of the constant region of a T-cell receptor (TcR), said two chains being the α and β chains or the γ and δ chains, and
   b. DNA coding for the variable regions of the heavy and light chains of an antibody specific for the predefined target antigen, such that, when expressed, one of said heavy and light chains of said antibody is attached to one of said two chains of said T-cell constant region and the other of said heavy and light chains of said antibody is attached to the other of said two chains of said T-cell constant regions, wherein said heavy and light chains are from an antibody specific towards tumor specific antigens, tumor associated antigens, viral antigens, or autoimmune disease type antigens.

24. A human mononuclear lymphocyte cell which expresses a chimeric receptor which permits said cell to direct its cellular immune response toward a predefined target antigen in a non-MHC restricted manner, said cell containing recombinant DNA encoding said chimeric receptor, said DNA consisting essentially of:
   a. DNA coding for an α, β, γ or δ chain of the constant region of a T-cell receptor (TcR), and
   b. DNA coding for the $V_H$ region of an antibody specific for the predefined target antigen.

25. A human mononuclear lymphocyte cell in accordance with claim 24, wherein said $V_H$ region is from an antibody specific towards a tumor-specific antigen, a tumor-associated antigen, a viral antigen, a modified self-antigen, a parasitic antigen, a bacterial antigen, a fungal antigen or an autoimmune disease type antigen.

26. A human mononuclear lymphocyte cell in accordance with claim 25, wherein said antibody is a monoclonal antibody reacting with a defined type of tumor cell.

27. A human mononuclear lymphocyte cell which expresses a chimeric receptor which permits said cell to direct its cellular immune response toward a predefined target antigen in a non-MHC restricted manner, said cell containing recombinant DNA encoding said chimeric receptor, said DNA comprising:
   a. DNA coding for the two chains of the constant region of a T-cell receptor (TcR), said two chains being the α and β chains or the γ and δ chains, and
   b. DNA coding for the variable regions of the heavy and light chains of an antibody specific for the predefined target antigen, such that, when expressed, one of said heavy and light chains of said antibody is attached to one of said two chains of said T-cell constant region and the other of said heavy and light chains of said antibody is attached to the other of said two chains of said T-cell constant regions.

28. A process of directing the immune response of a patient toward a predefined target antigen, comprising the steps of:
   (1) transfecting mononuclear lymphocyte cells with a recombinant DNA comprising
      (a) DNA coding for an α, β, γ or δ chain of the constant region of a T-cell receptor (TcR), and
      (b) DNA coding for the $V_H$ region of an antibody specific for the predefined target antigen, and
   (2) inoculating the patient with the transfected lymphocyte cells.

29. A process in accordance with claim 28, wherein the mononuclear lymphocyte cell is a T-killer cell.

30. A process in accordance with claim 28, wherein the mononuclear lymphocyte cell is one which has been isolated from the patient to be treated and wherein said inoculating step comprises reinoculating the transfected cell into the patient from which it was isolated.

31. A process in accordance with claim 30, wherein DNA encoding said $V_H$ region is that of an antibody specific for a defined type of tumor or HIV-infected cell.

32. A process in accordance with claim 28, wherein said DNA of (a) encodes the two chains of the constant region of a TcR, said two chains being the α and β chains or the γ and δ chains, and wherein said DNA of (b) encodes the variable regions of the heavy and light chains of an antibody specific for the predefined target antigen, such that, when expressed, one of said heavy and light chains of said antibody is attached to one of said two chains of said T-cell constant regions and the other of said heavy and light chains of said antibody is attached to the other of said two chains of said T-cell constant regions.

33. A process for producing a vector containing a DNA sequence coding for an antibody variable region and a DNA sequence coding for the constant region of a T-cell receptor (TcR), comprising:
   preparing a TcR expression cassette containing regulatory regions and the DNA encoding the constant region of a TcR;
   amplifying by polymerase chain reaction an antibody variable region of known or unknown sequence using primers composed of consensus sequences of $J_H$ or $J_C$ for the 3' end and poly(dG) tail for the 5' end; and
   cloning the amplified antibody variable regions directly into said TcR expression cassette.

* * * * *

UNITED STATES PATENT AND TRADEMARK OFFICE
CERTIFICATE OF CORRECTION

PATENT NO. : 5,906,936

DATED : May 25, 1999

INVENTOR(S) : Zelig Eshhar, et al.

It is certified that error appears in the above-identified patent and that said Letters Patent is hereby corrected as shown below:

Column 3, line 1, change "FIG. 2" to --FIGS. 2A-2B--.

Column 3, line 16, change "FIG. 5" to --FIGS. 5A-5B--.

Column 3, line 19, change "(A)" to --FIG. 5A--.

Column 3, line 19, change "(B)" to --FIG. 5B--.

Figure 9A:
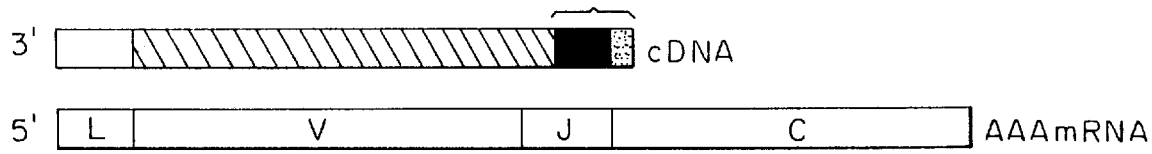
FIG. 9 describes the procedure used to amplify and clone $V_H$ and $V_L$ using the "Anchored PCR" technique.
Figure 9B:
Figure 9C:
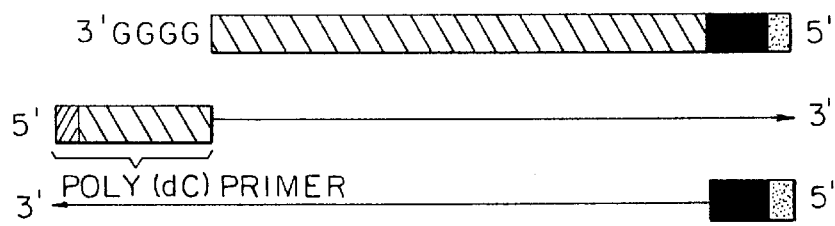
Figure 10:
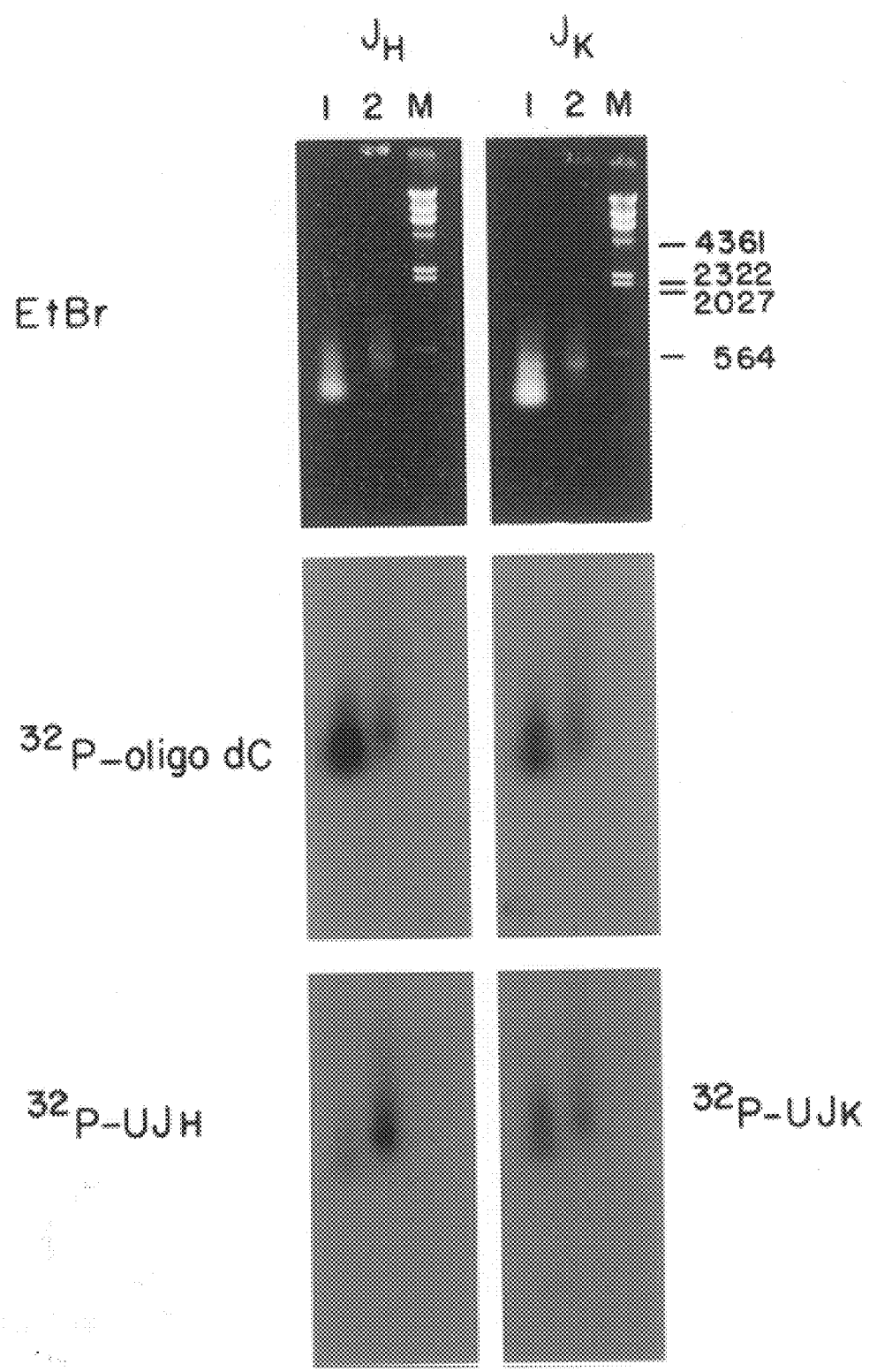
FIG. 10 shows cRNA products of mRNA amplified from a hybridoma. Probes used in the Southern analysis: (dc) (middle) and Universal $J_H$ and $J_K$ primers (lower).

Column 3, line 33, change "FIG. 9" to --FIGS. 9A-9C--.

Column 6, line 17, change "FIG. 9" to --FIGS. 9A-9C--.

Column 7, line 37, change "(FIG. 2)" to --(FIGS. 2A-2B)--.

UNITED STATES PATENT AND TRADEMARK OFFICE
CERTIFICATE OF CORRECTION

PATENT NO. : 5,906,936
DATED : May 25, 1999
INVENTOR(S) : Zelig Eshhar; Gideon Gross; Tova Waks;

It is certified that error appears in the above-identified patent and that said Letters Patent is hereby corrected as shown below:

```
Column 13, line 5 (claim 14, line 1), change "T-killer"
to --lymphocyte--.
Column 13, line 9 (claim 15, line 1), change "T-killer"
to --lymphocyte--.
Column 13, line 13 (claim 16, line 11), change "T-killer"
to --lymphocyte--.
Column 13, line 17 (claim 17, line 11), change "T-killer"
to --lymphocyte--.
Column 13, line 20 (claim 18, line 11), change "T-killer"
to --lymphocyte--.
```

Signed and Sealed this

Nineteenth Day of October, 1999

Attest:

Attesting Officer

Q. TODD DICKINSON

Acting Commissioner of Patents and Trademarks